United States Patent [19]

Rudler et al.

[11] 4,414,998
[45] Nov. 15, 1983

[54] AIR GAP SYSTEM TO MAINTAIN PURE LIQUID SUPPLIES

[75] Inventors: Helmut Rudler, York; Ralph J. Williams, New Oxford, both of Pa.

[73] Assignee: Dentsply Research & Development Corp., Milford, Del.

[21] Appl. No.: 291,893

[22] Filed: Aug. 11, 1981

[51] Int. Cl.$^3$ ............... E03C 1/10; F16K 24/00; F16L 55/07
[52] U.S. Cl. ............... 137/216; 137/312; 137/414; 137/432; 137/436; 137/444; 137/571; 137/592
[58] Field of Search ............... 137/216, 101.27, 312, 137/414, 428, 430, 432, 436, 444, 571, 592

[56] References Cited

U.S. PATENT DOCUMENTS

| | | | |
|---|---|---|---|
| 1,590,321 | 6/1926 | Sartakoff | 137/428 |
| 2,111,614 | 3/1938 | Cox | 137/215 |
| 2,195,797 | 4/1940 | Groeniger | 137/592 |
| 2,277,878 | 3/1942 | Morris | 137/216 |
| 2,409,890 | 10/1946 | Owens | 137/216 |
| 2,581,043 | 1/1952 | Owens | 137/216 |
| 2,655,171 | 10/1953 | Cantor | 137/218 |
| 2,706,998 | 4/1955 | Bletcher et al. | 137/216 |
| 2,941,542 | 6/1960 | Jacobson | 137/218 |
| 2,986,155 | 5/1961 | Doyle | 137/414 |
| 3,180,352 | 4/1965 | Kersten et al. | 137/218 |
| 3,194,258 | 7/1965 | Grant | 137/414 |
| 3,482,313 | 12/1969 | Stram | 433/92 |
| 3,713,457 | 1/1973 | McInnis et al. | 137/218 |
| 3,930,516 | 1/1976 | Flinner et al. | 137/312 |
| 4,245,989 | 1/1981 | Folkenroth et al. | 433/92 |

FOREIGN PATENT DOCUMENTS 2801 of 1886 United Kingdom ............... 137/428

Primary Examiner—George L. Walton
Attorney, Agent, or Firm—C. Hercus Just

[57] ABSTRACT

A safety air gap system for an exemplary high volume evacuator having a water-sealed pump to provide suction thereto and including a gray water discharge from the pump to a drain, the system including a closed housing adapted to be mounted at a higher level than the evacuator, a reservoir for fresh water in the housing terminating a predetermined distance below the top, a coaxial pair of inner and outer tubes extending upward from the bottom of the reservoir and terminating above the top of the reservoir, the lower end of the inner tube receiving municipal water for discharge at the top to the outer tube which discharges the water at the lower end to the reservoir as controlled by a float-operated valve between the upper ends of the tubes, the housing having in one sidewall an outlet port connectable to a drain at a level below the top of the reservoir to prevent accidental filling of the housing with water in the event of a malfunction of the system, and an air gap opening positioned in a sidewall of the housing at a level above the outlet opening but no higher than the top of the reservoir to permit any water overflowing from the reservoir to discharge therethrough without creating suction in the event of a stoppage of the outlet opening to a drain.

5 Claims, 2 Drawing Figures

AIR GAP SYSTEM TO MAINTAIN PURE LIQUID SUPPLIES

BACKGROUND OF THE INVENTION

The present invention primarily is for use with a high volume evacuator, especially of the type employed in dental offices to withdraw from the oral cavity of patients flushing and cooling water, mouth fluids, and debris resulting from various dental operations, such as metal chips, tooth fragments and grindings, and the like. This type of fluid is known as "gray water" to signify that it is impure and not to be confused with fresh water, such as that obtained from a municipal supply provided in a dental operatory. Other uses are set forth below.

One widely used type of high volume evacuator is shown at least in basic principles in prior U.S. Pat. Nos. 3,482,313, to G. H. Stram, dated Dec. 9, 1969 and 4,245,989 to Richard P. Folkenroth et al, dated Jan. 20, 1981.

Essentially, the high volume evacuating system illustrated in the aforementioned patents includes a liquid seal pump which, at all times, must have a residue of liquid therein to operate it, such as by maintaining the pump primed, and while, at least initially, the priming water is clear fresh water, after the system has been operating for a certain period, the sealing water may constitute gray water which is of an unpure nature as far as human consumption is concerned. Nevertheless, the system is connected with a municipal supply of fresh water, and particularly, where systems of this type are located in high-rise buildings, it sometimes happens that the pressure on the municipal supply water to an operatory may dissapear due to certain failures, such as the municipal water pump for the building to be deactivated or otherwise malfunction, under which circumstances, it is possible for a vacuum to exist in the fresh water supply, and thus it is conceivable and actually possible for such suction to draw gray water from the pump or other residues of gray water in the high volume evacuator system and thereby contaminate the municipal water supply to the operatory.

To prevent such phenomenon from occurring, certain municipalities have required vacuum breakers or other suitable devices to be employed in lines associated with fresh water or municipal supply and, in an effort to comply with such requirements, the present invention has been developed to provide a relatively inexpensive means for preventing suction accidentally being imposed upon the fresh water supply, under the circumstances described above, as well as other situations described below.

Vacuum breaker structure per se are quite old. Typical examples of them are represented by the following U.S. Pat. Nos.: 2,655,171, Cantor, Oct. 13, 1953; 3,180,352, Kersten et al, Apr. 27, 1965; 3,713,457, McInnis et al, Jan. 30, 1973.

The present invention also includes float-operated valves, similar to those used in the water tank associated with toilet commodes and also for purposes of preventing siphoning of water from the tank into the fresh water supply connected to the tank. Essentially, structures of this type per se also are old and typical examples of these are illustrated in prior U.S. Pat. Nos. 2,111,614 to Cox, dated Mar. 22, 1938 and 2,941,542 to Jacobson, dated June 21, 1960.

While the present invention employs certain characteristics of the structure shown in the aforementioned prior patents, it, nevertheless, is directed to an overall different system than shown in the prior structures, details of which are set forth hereinafter.

SUMMARY OF THE INVENTION

It is among the principal objects of the invention to provide, in conjunction with high volume evacuator units designed to withdraw flushing water and debris, mouth fluids, and the like resulting from dental operations in operatories, safety means to prevent the possibility of contaminated water from the pumps of high volume evacuator units being entrained or comingled with fresh municipal supply water, which also is required in the operation of such high volume evacuator units, said safety means including a tank-like housing provided with an internal reservoir which terminates a predetermined distance from the top of a housing and including a coaxial pair of inner and outer tubes of different diameters nested in said housing and extending vertically from the bottom thereof to a predetermined distance substantially above the top of the reservoir, said inner and outer tubes respectively receiving a supply of municipal fresh water and discharging the same to the bottom of the reservoir for delivery of such fresh water therefrom to the pump of the high volume evacuator unit, the principal feature of the invention comprising a flow control valve located at the upper end of said coaxial tubes to control the flow of such water by means of a float operable vertically in the reservoir and connected to the valve for operation thereof to determine a normal level of fresh water in the reservoir, the housing having in one side thereof, at a level substantially below the top of the reservoir, an outlet to a drain to prevent accidentally filling the housing with water in the event of a malfunction of the system, and also providing an air gap opening in one wall of the housing at a level above that of said outlet in the housing but no higher than the top of said reservoir, to permit overflow water from the reservoir to discharge from said housing in the event of a malfunction of said outlet to a drain.

It is another object of the invention to provide said housing and reservoir in the form of a pair of coaxial cylinders with the top of the reservoir cylinder being substantially below the top of said housing and both cylinders extending upward from a common bottom.

It is a further object of the invention to form said float as a hollow body having a tubular guide extending axially between the upper and lower ends thereof and surrounding the outer tube of said coaxial pair of inner and outer tubes for guidance therealong.

Still another object of the invention is to provide on the upper end of the outer tube of said pair of inner and outer tubes a support to which a lever is pivotally connected, and also including means connecting one end of said lever to a movable valve member in the control valve and link means connecting the other end of said lever to said float.

Details of the foregoing objects and of the invention, as well as other objects thereof, are set forth in the following specification and illustrated in the accompanying drawings comprising a part thereof.

DETAILED DESCRIPTION OF THE PREFERRED EMBODIMENT

Figure 1:
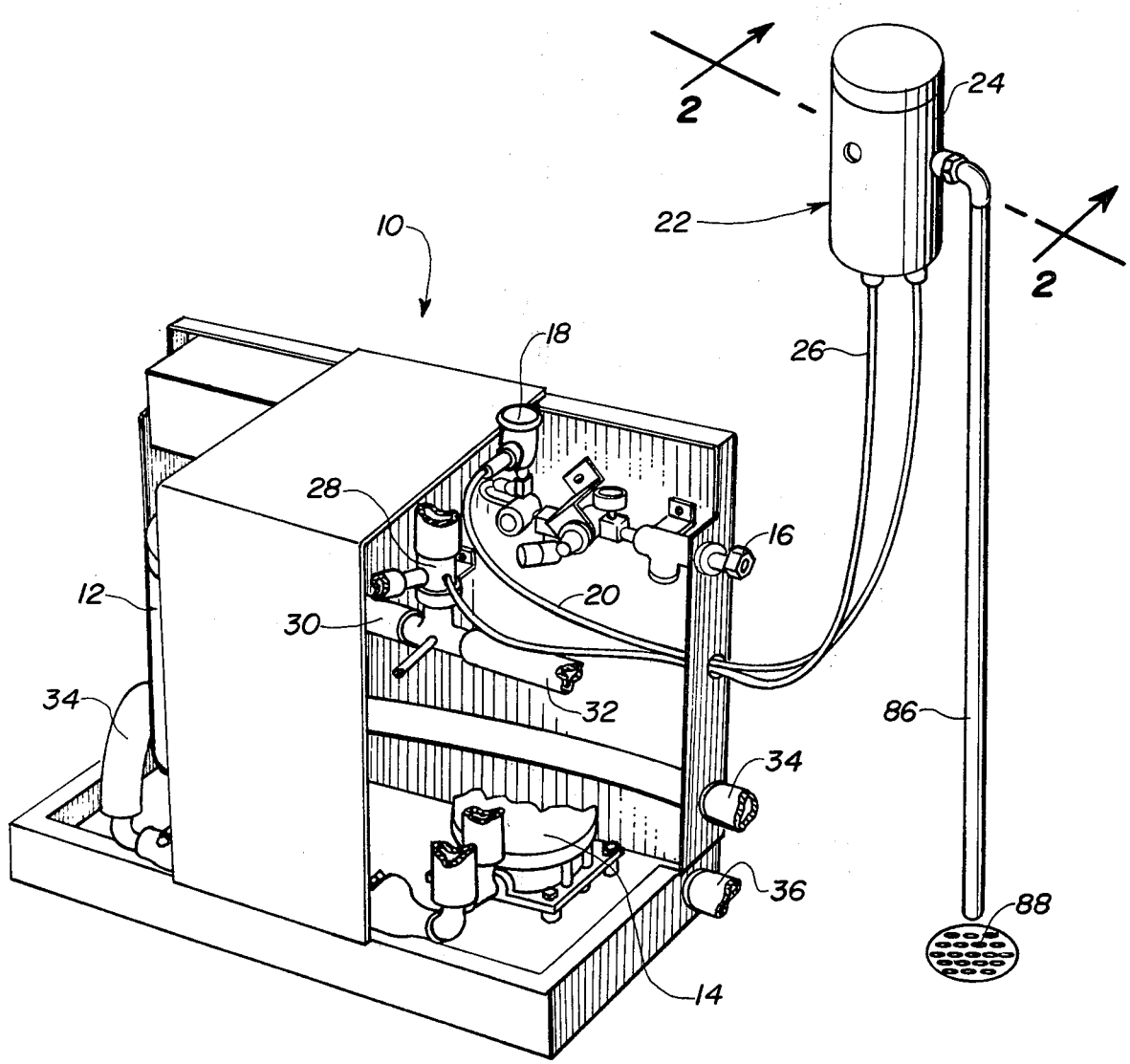
FIG. 1 is a perspective view of an exemplary high volume evacuator unit from which part of the housing has been removed to illustrate details thereof and portions of said details being broken away to simplify the illustration, and including an exterior perspective view of the air gap unit associated with a high volume evacuator unit.

Referring to FIG. 1, an exemplary high volume evacuator unit 10 is illustrated with part of the exterior housing removed. Said unit is of the type which includes a pair of liquid sealed pumps 12 and 14, the upper portion of pump 14 being broken away. For details of said pumps, attention is directed to aforementioned U.S. Pat. No. 3,482,313 to Stram, especially FIGS. 3–6 thereof. It is essential that said pumps be primed at all times by including a residual amount of water in the impeller chambers in the pumps and a common way of maintaining such priming supply is to have at least part of the so-called "gray water" of the evacuating system remain in said impeller chamber. The term "gray water" is used to indicate partly contaminated water comprising flushing water withdrawn from the oral cavity of patients, together with debris resulting from dental operations, such as chips and particles of teeth, fillings, and otherwise. As indicated above, it is essential that none of such contaminated water be introduced by suction or otherwise to the municipal supply of fresh water which is connected to the unit 10 for proper operation thereof.

Figure 2:
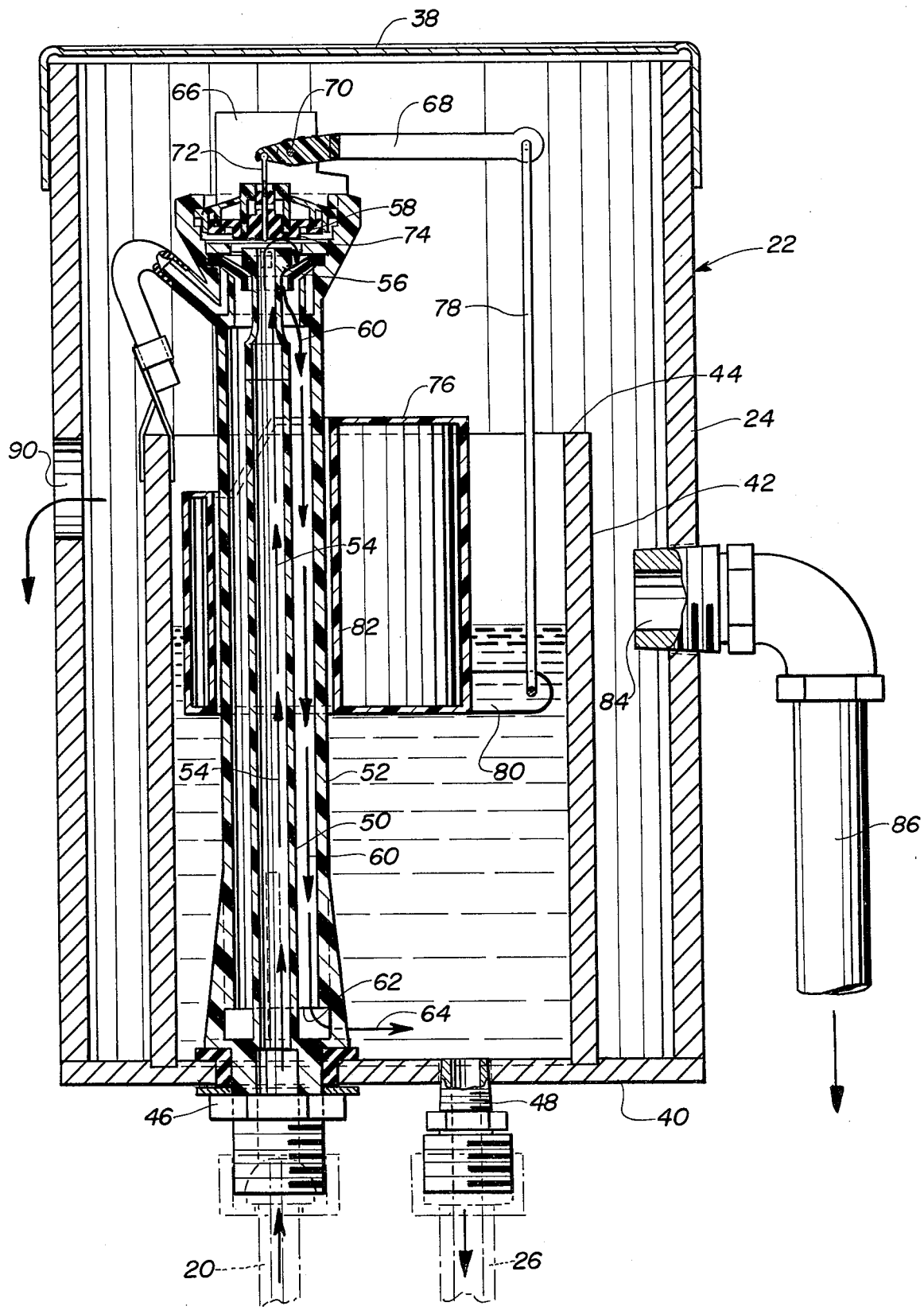
FIG. 2 is an enlarged vertical sectional view of the air gap unit shown in FIG. 1, as seen on the line 2—2 thereof.

The evacuating unit 10 includes an inlet 16 for municipal fresh water. The fresh water passes through a number of pressure control and indicating units extending inward from the inlet 16, as clearly shown in FIG. 1, and is discharged through vacuum breaker 18 to a first conduit 20, which leads to the bottom of an air gap unit 22, which includes an outer housing 24, details of which are best shown in FIG. 2. Municipal fresh water is discharged from air gap unit 22 through a second conduit 26 to an orifice unit 28, shown in FIG. 1, and from which the municipal fresh water is delivered to the pumps by conduits 30 and 32, which are shown fragmentarily.

The evacuator unit 10 also includes an air-water separator, not shown, to which gray water discharges from the pumps, and in turn, discharges to a sewer connection. Conduit 34, shown in FIG. 1, carries said gray water from the pump to the air-water separator and still another conduit 36, shown fragmentarily in FIG. 1, is a suction line to the pumps from the operatories serviced by the evacuating unit 10.

It has been found that through malfunction, accident, or otherwise, the supply of municipal fresh water to dental operatories sometimes fails. Under such circumstances, particularly in high-rise buildings, where pumps are required to maintain the municipal fresh water supply under pressure to operatories located at high elevations in such buildings, it has been found that when the water pressure fails, suction can be produced in the water supply lines and under such circumstances where high volume evacuator units of the type described above are included in such operatories, there is a possibility that gray water existing in the evacuator unit can be drawn by suction into the municipal fresh water supply lines, whereby a number of municipalities now have ordinances requiring mechanism to be utilized with such evacuating units which will prevent any possibility of such contamination of the municipal water supply. The present invention has been developed to meet the necessary requirements of such municipalities and the details of the air gap unit 22, which is for such purpose, are described as follows:

Referring to FIG. 2, aforementioned outer housing 24 preferably is tubular and of a predetermined height. It includes a cover 38 and a bottom 40. Within the outer housing 24 is a reservoir 42, which preferably is cylindrical and the lower end thereof is fixedly secured in waterproof nature to the bottom 40. The upper end 44 of reservoir 42 is spaced a substantial distance from the upper end of the outer housing 24, as clearly shown in FIG. 2, and the cylindrical reservoir also preferably is coaxial with outer housing 24, as clearly shown in FIG. 2.

Bottom 40 is provided with an inlet nipple 46 to which first conduit 20 is connected and through which municipal fresh water is delivered to the air gap unit 22, particularly to the reservoir 42 thereof, by means described in detail hereinafter. Similarly, bottom 40 is provided with a discharge nipple 48 to which second conduit 26 is connected, as shown in FIG. 2, for purposes of delivering municipal fresh water in reservoir 42 to the pump units as described hereinabove. For purposes of controlling the volume of municipal fresh water normally maintained within the reservoir 42, said reservoir is provided with a coaxial pair of tubes comprising inner tube 50 and outer tube 52. Inner tube 50 receives municipal fresh water from first conduit 20 by being connected to nipple 46, the flow of such water therein being indicated by directional arrows 54, which extend upwardly, as seen in said figure. The water flows to the upper end 56 of inner tube 50 and then is redirected through control valve 58 into the upper end of the outer tube 52 for movement of the water downwardly therein, as indicated by the directional arrow 60. As shown in FIG. 2, the lower end portion of the outer tube 52 is provided with a series of laterally extending outlet openings 62 through which the municipal fresh water passes into the reservoir 42, as indicated by arrow 64, as determined by the operation of control valve 58, which is as follows:

The upper part of the outer tube 52 is provided with an upstanding support 66 for purposes of mounting the lever 68 by means of a pin 70, which extends through the lever intermediately of the opposite ends thereof. The left-hand end of lever 68, as viewed in FIG. 2, is connected to a valve-operating rod 72 for actuating the movable valve member 74, which is adapted to abut the upper end 56 of the inner tube 50 for purposes of stopping the flow of water from the inner tube to the outer tube, as actuated by the float 76. The opposite end of lever 68 is connected by link 78 to an ear 80 projecting laterally from the lower end of float 76.

It will be noted that the float 76 is hollow and is provided with a tubular guide 82, the opposite ends of which are fixed to the upper and lower ends of the hollow float 76. The tubular guide 82 surrounds the outer tube 52 for guided movement vertically thereon and sufficient clearance is provided between the inner surface of tubular guide 82 and outer tube 52 to permit ready movement of the float vertically. The floating capacity of float 76 and the length of link 78 are calculated to close the control valve 58 when a desired amount of water has been discharged into reservoir 42 for delivery through the second conduit 26 to the evacuator unit when such supply is required, as when the evacuator unit is functioning in response to demands from the operatory units connected thereto.

It has been indicated hereinabove that there are occasions when the delivery of municipal fresh water to an operatory unit may be interrupted in one way or another so that instead of municipal fresh water being delivered through the first conduit 20 to the reservoir 42, suction will actually be developed in the first conduit 20 and because of the connection of the second conduit 26 to gray water in the circulating system of the evacuator unit 10, it is conceivable that the suction in the first conduit 20 can cause gray water to be drawn down through said conduit 20 and thus, contaminate the municipal fresh water supply. However, in view of the height of the coaxial pair of inner and outer tubes 50 and 52 above the upper end of reservoir 42, this cannot occur, and prevention of such occurrence is additionally augmented by the following means. Due to malfunctioning of the system by any means under which water, especially gray water, runs into the reservoir 42 and overflows the same, it will be seen that one wall of the outer housing 24 is provided with a safety discharge port 84 at a level appreciably below the top 44 of the reservoir 42 and said port 84 includes a drain pipe 86, the lower end of which is adjacent a drain 88, located, for example, in the floor of a dental operatory or service room associated with the operatory. In the event the drain pipe 86 should for any reason become clogged, however, a further safety means is afforded by an air gap opening 90 in another portion of the wall of outer housing 24, as shown at the left side of FIG. 2. The opening 90 is at a level above that of the discharge port 84, but is not higher than the top rim 44 of reservoir 42, whereby if overflow of the reservoir continues, the water discharged from reservoir 42 will exit through air gap opening 90 and discharge onto the floor of the room where the air gap unit 22 is located and thereby, provide further safety means to prevent contamination of the municipal fresh water supply connected to the air gap unit 22.

From FIG. 2, it will be seen from the shading of the cross-sectioned tubes 50 and 52, control valve 58, and float 76 preferably may be made expeditiously and conveniently by molding the same from suitable plastic material, preferably of a relatively rigid nature. Further, although the outer housing 24 and reservoir 42 also may be made from plastic materials, it is preferred that the same be formed from suitable metal for strength and durability.

The system set forth in the foregoing description is illustrative of a specific primary use in which the air gap system of the invention may be employed to great advantage. However, there are other uses and equipment in which said air gap system may be employed to equal advantage for the principal purpose of preventing contaminated liquids from entering a supply of pure, uncontaminated water, municipal or otherwise. For example, water supplied to dental laboratories for use in baths to boil-out wax from models conceivably can accidentally create a vacuum capable of drawing the bath liquid into a municipal supply; vending machines which discharge liquids into cups handled by the public are at least remotely subject to having the municipal supply entrain contamination from a cup into the discharge nozzle by suction; similarly, ice makers, dental units, prophylaxis dental units, X-ray processing equipment, various hospital equipment, and industrial equipment, such as plating baths and the like, when each is connected to a municipal water supply, conceivably can be connected in fluid systems in such manner that suction can occur, usually by accidental loss of pressure, and thereby cause contaminating liquids to enter municipal water supplies. Hence, the system of the present invention can be incorporated to advantage in the water supply conduits of the foregoing exemplary systems and equipment, in addition to high volume evacuator systems as specifically described in detail hereinabove.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

We claim:

1. An air gap unit and system comprising in combination:
   a. a housing,
   b. a reservoir in said housing of less area than said housing and extending upward from the bottom of the housing and terminating a predetermined distance from the top of said housing,
   c. a coaxial pair of inner and outer tubes of different diameters nested in said housing and extending vertically from the bottom of said housing, the upper ends of said tubes extending a predetermined distance substantially above the top of said reservoir,
   d. first conduit means extending from the lower end of said inner tube to a municipal fresh water supply,
   e. second conduit means connectable to the bottom of said reservoir for delivery of fresh water from said reservoir to a mechanism requiring the same,
   f. a flow control valve at the upper end of said coaxial tubes to control the flow of water from said top of the inner tube to the top of the outer tube,
   g. the lower end of the outer tube having fresh water discharge opening means to permit the flow of fresh water therefrom into said reservoir,
   h. a float operable vertically in said reservoir and connected to said valve for operation thereof to determine a normal level of fresh water in said reservoir,
   i. said housing having in one sidewall thereof at a level substantially below the top of said reservoir an outlet to a drain to prevent accidentally filling the housing with water in the event of a malfunction of the system, and
   j. an air gap opening in one wall of said housing at a level above that of said outlet in said housing but no higher than the top of said reservoir to permit overflow water from said reservoir to discharge from said housing in the event of a malfunction of said outlet.

2. The air gap unit and system according to claim 1 further characterized by said housing and reservoir being cylindrical and coaxial for compactness.

3. The air gap unit and system according to claim 2 in which said housing and reservoir extend upward from a common bottom.

4. The air gap unit and system according to claim 1 further characterized by said float comprising a hollow body having a tubular guide extending axially between the upper and lower ends thereof and surrounding the outer tube of said coaxial pair of inner and outer tubes for guidance therealong.

5. The air gap unit and system according to claim 4 further including a support on the upper end of the outer tube of said pair of inner and outer tubes, a lever pivotally connected to said support, means connecting one end of said lever to a movable valve member in said control valve, and link means connecting the other end of said lever to said float.

* * * * *